United States Patent [19]

Dehnert

[11] 4,015,596
[45] Apr. 5, 1977

[54] APPARATUS FOR DETECTING AND INDICATING ELECTRICAL BODY POTENTIALS

[75] Inventor: Heinz Dehnert, Freiburg, Breisgau, Germany

[73] Assignee: Hugo Sachs Elektronik Kommanditgesellschaft, Hugstetten-March, Germany

[22] Filed: June 25, 1975

[21] Appl. No.: 590,369

[30] Foreign Application Priority Data

Mar. 29, 1975 Germany .................. 7510018[U]

[52] U.S. Cl. .............. 128/2.06 R; 128/2.06 F; 128/2.1 E; 128/DIG. 4

[51] Int. Cl.² .................................. A61B 5/04

[58] Field of Search ............. 128/2.05 R, 20.6 A, 128/2.06 B, 2.06 E, 2.06 F, 2.06 G, 2.06 R, 2.06 V, 2.1 B, 2.1 E, 2.1 M, DIG. 4, 404, 405, 410, 418

[56] References Cited

UNITED STATES PATENTS

| | | | |
|---|---|---|---|
| 3,279,468 | 10/1966 | Le Vine | 128/410 |
| 3,547,107 | 12/1970 | Chapman et al. | 128/2.06 A |
| 3,702,113 | 11/1972 | Blockley | 128/2.06 E |
| 3,848,582 | 11/1974 | Milani et al. | 128/2.06 R |

Primary Examiner—William E. Kamm
Attorney, Agent, or Firm—William D. Hall; Goeffrey R. Myers

[57] ABSTRACT

A device for measuring the potential across two points on the human body, comprising a box-like structure having distinct side walls, one of which includes the screen of a cathode ray tube. On each of first and second adjoining side walls of the box-like structure there are two spaced body-contacting electrodes adapted to be pressed against a human body to measure the potential across the two points on the human body corresponding to the position of said electrodes thereon. The box-like structure includes internal circuitry of a type well known in the prior art for measuring the potential between said electrodes and displaying the same on said cathode ray tube. The two electrodes on one face of the box wrapped around an edge of the box to thus form electrodes on another face, so that the box-like structure can be placed in either of two positions on the human body, to give two viewing positions for the cathode ray tube. One of said two faces of the box is opposite to the end of the box which includes the screen of the cathode ray tube. A strap is provided whereby the box-like structure can be strapped to the human body, with one of said electrode-carrying side walls in intimate contact with the body, so that a continuous reading can be easily taken.

5 Claims, 3 Drawing Figures

APPARATUS FOR DETECTING AND INDICATING ELECTRICAL BODY POTENTIALS

BACKGROUND OF THE INVENTION

The prior art shows a device for the detection and indication of the heart action potential of a patient. The device includes a box-shaped housing equipped with three electrodes arranged on its bottom side. This apparatus is intended to be placed onto the chest of a patient in such a way that the electrodes make contact with the patient's skin. On the side of the housing opposite the side equipped with the electrodes is the screen of a cathode ray tube on which the changes in the reading of the body potential can be observed.

Such prior art devices are described in U.S. Pat. No. 3 858 576 of Dehnert et al.

These prior art devices have the disadvantage that, during use, the apparatus must be held in place by hand. Consequently, it is primarily suitable only for short, quick diagnosing of a patient. Furthermore, such instruments are adapted only for the reading of ECG potentials.

It is frequently necessary, especially during the transport of a patient, to continuously monitor the changes in his action potentials. This includes monitoring of not only heart action potentials, but also brain action potentials and muscle action potentials.

BRIEF SUMMARY OF THE INVENTION

Underlying the present invention, therefore, is the need for an improved apparatus of the aforementioned type which is adapted to be used for quick diagnoses, as well as for continuous application, as for example, during the transport of a patient. In the latter case, it is necessary that the device remain in contact with the body of a patient, without the need for an attendant to hold it.

It is therefore an object of the present invention to provide a monitoring apparatus, the internal arrangement of which is similar to the above-mentioned prior art type, but in which the housing carries at least two electrodes, each of which has a body-contacting face wrapped around an edge of the housing so as to be usable on each of two adjacent sides of the housing; the housing is further equipped with tie straps for the attachment of the apparatus to the body of a patient. Said edge is opposite the side of the housing which includes the screen of the cathode ray tube.

BRIEF DESCRIPTION OF THE DRAWING

Further special features and advantages of the invention will become apparent from the description following below, when taken together with the accompanying drawing which illustrates, by way of example, certain embodiments of the invention, represented as follows.

DESCRIPTION OF THE PREFERRED EMBODIMENTS

Figure 1:
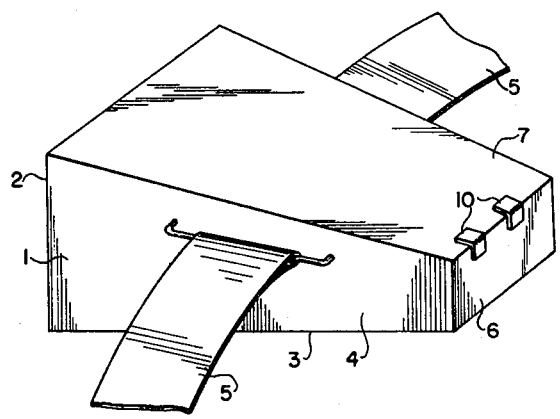
FIG. 1 is a perspective view of a body potential indicating apparatus embodying the invention, the apparatus being positioned upside down.

The present invention includes any conventional, suitable arrangement for monitoring electrical body potentials of a patient. For example, see the references to the prior art arrangement referred to near the middle of page 2 above, which shows the internal electrical circuitry of the apparatus. The present device employs that same electrical circuit arrangement of the prior art. The inventive feature of the apparatus is included in the external housing, which may be described as follows:

The apparatus of the invention is represented by a block-shaped housing 1, having tie straps 5 extending from both lateral sides 4 thereof, for the attachment of the device to the body of a patient. On the front side 2 of the housing (FIG. 3) is arranged, for example, a conventional display screen 11 of a cathode ray tube. A conventional visual recording device (not shown), giving graphically a continuous picture of the body potential readings, may be arranged in addition to the cathode ray tube, or may take the place of the latter. Such a recording device may alternatively also be arranged on the top side 3 of the housing 1.

In the form of the invention shown in FIG. 1, two electrodes 10 are disposed on the housing 1, each of the electrodes extending along each of adjacent sides of the housing 1. In the case of a quick spot diagnosis, for which the apparatus is held by hand, those portions of the electrodes 10 which extend on the back side 6 of the housing contact the body. If, on the other hand, the apparatus is attached to the body of a patient, by means of tie straps 5, then the body of the patient is in contact with those portions of the electrodes 10 which extend on the bottom side 7 of the housing. The two electrodes 10 thus serve a dual purpose.

Figure 2:
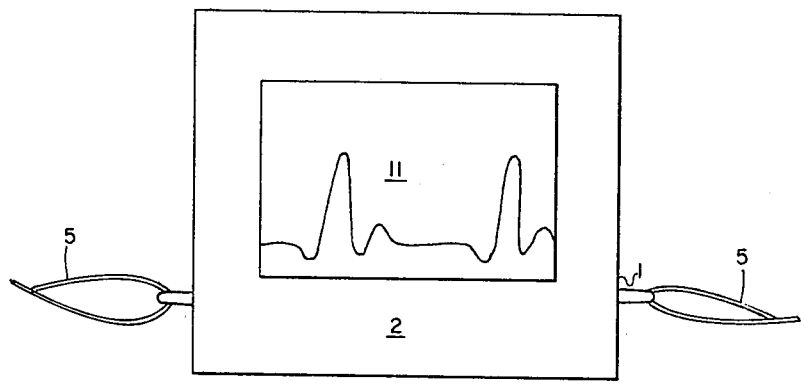
FIG. 2 is an end view of one face of the invention.
Figure 3:
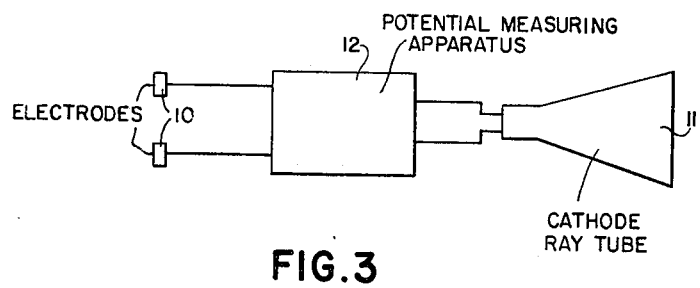
FIG. 3 is a block diagram of the electrical circuitry of the apparatus.

FIG. 3 shows, in diagram form, electrodes 10 which wrap around the edge connecting sides 6 and 7 of the housing, which electrodes feed prior art mechanism 12, which measures body potential between the two electrodes 10 respectively and feeds signals to a cathode ray tube to indicate the body potentials on the screen 11 thereof, as shown in FIG. 2.

The reading electrodes 10, respectively, are designed to detect various kinds of electrical body potentials, i.e., ECG potentials, EEG potentials, and EMG potentials.

The electrodes themselves may be either metallic, using steel or silver, or they may be of graphite or of a semi-conductor material. The surfaces of the electrodes are preferably coarse, having for example sharp contact spikes, obtained as a result of a special electrolytic treatment, which spikes are capable of painlessly penetrating the epidermis, thereby creating a contact of good conductivity, so as to eliminate the previously necessary complicated operation of wetting the electrodes. The proposed apparatus is particularly suited for use by rescue squads, in medical emergency situations.

It should be understood, of course, that the foregoing disclosure describes only two embodiments of the invention and is intended to cover all changes and modifications of this example of the invention which fall within the scope of the appended claims.

I claim:

1. Apparatus for the detection and indication of electrical body potentials having a generally box-like structure, a cathode ray tube in said box-like structure, said cathode ray tube having a face constituting at least a part of one of the side walls of said box-like structure, first and second electrode means adapted to contact a human body in the respective places between which the body potential is to be measured, and means responsive to any potential difference between said first and second electrodes, controlling said cathode ray tube so that the latter indicates said body potentials, characterized by said first and second electrode means comprising first and second electrodes on each of two sides of the box-like structure, said two sides being different from the side wall that includes the face of the cathode ray tube, and said first and second electrode means comprising first and second electrodes each of which extends around the corner of the box that connects said two sides.

2. Apparatus for the detection and indication of electrical body potentials as defined in claim 1, in which one of said two sides is a side of the box-like structure opposite to the side that includes the cathode ray tube face.

3. Apparatus for the detection and indication of electrical body potentials as defined in claim 2, in which said two sides comprise two adjoining sides of the box-like structure.

4. Apparatus for the detection and indication of electrical body potentials as defined in claim 1, in which one of said two sides is a side adjoining the side which includes the face of said cathode ray tube, and strap means carried by said box-like structure for strapping the box-like structure to the human body, with said one of said two sides in contact with the human body, so that two of said electrodes contact spaced parts of the human body.

5. Apparatus for the detection and indication of electrical body potentials as defined in claim 4, in which said first and second electrode means also includes two electrodes on the side of the box-like structure opposite the side which includes the face of said cathode ray tube.

* * * * *